United States Patent [19]

Buckles et al.

[11] 4,326,025

[45] Apr. 20, 1982

[54] ANTI-HEMOLYTIC AGENT EMULSIONS AND THE USE THEREOF

[75] Inventors: Richard G. Buckles, Basel, Switzerland; Jan W. Garber, McHenry, Ill.

[73] Assignee: Baxter Travenol Laboratories, Inc., Deerfield, Ill.

[21] Appl. No.: 105,468

[22] Filed: Dec. 19, 1979

[51] Int. Cl.³ .................. A01N 1/02; A61K 35/14
[52] U.S. Cl. .................................... 435/2; 150/1; 206/438; 424/101
[58] Field of Search ........................... 435/2; 424/101

[56] References Cited

PUBLICATIONS

Nakaura et al.–Chem. Abst. vol. 82, (1975), p. 164,949K.

Valeri et al.–Chem. Abst. vol. 83, (1975) p. 76328X.

*Primary Examiner*—Sam Rosen
*Attorney, Agent, or Firm*—Paul C. Flattery; John A. Caruso; Garrettson Ellis

[57] ABSTRACT

Blood may be stored in vitro for a period of days at a reduced temperature in the container which also includes a sufficient quantity of an emulsion of anti-hemolytic agent to cause a reduction in the hemolysis of the stored blood, when compared with blood under similar storage conditions to the absence of the emulsion. Preferably, the emulsion includes a fatty ester containing at least two ester linkages each comprising a fatty hydrocarbon group, emulsified with sufficient hemo-compatible surfactant to stabilize the emulsion.

34 Claims, No Drawings

ANTI-HEMOLYTIC AGENT EMULSIONS AND THE USE THEREOF

BACKGROUND OF THE INVENTION

In copending U.S. Application Ser. No. 955,060 filed Oct. 26, 1978 by Ulrich d. Geissler, et al. for "Blood Compatible Polymers and Medical Devices Made Therefrom" it is taught that, most surprisingly, common plasticizers for plastic materials such as di-2-ethylhexylphthalate and di-2-ethylhexyladipate are antihemolytic agents. In their presence, stored blood exhibits significantly lowered hemolysis over the period of storage than in the absence of such materials.

While the commercially-available blood bags have been made of polyvinyl chloride formulations which include di-2-ethylhexylphthalate, other candidate blood bag materials were free of such ester-type plasticizers, intentionally so, because it had been suggested from some experts that the ester-type plasticizers were undesirable, and should not be present in the plastic containers used for storage of blood.

It most surprisingly turned out that the various materials which were free of the ester-type plasticizers exhibited an undesirably high plasma hemoglobin content after, for example, 21 days of storage, indicating that the lysis rate of the red blood cells was high.

After this phenomenon was identified, further studies indicated that it was apparently necessary to incorporate the ester plasticizer into plastic material in contact with the stored blood, to get the anti-hemolytic effect. This could be done either by formulating the material into the blood container itself, or a plastic insert member to the container in which the insert member contains the estertype plasticizer in accordance with copending U.S. patent application Ser. No. 954,969, filed Oct. 26, 1978 by Henry W. Collins and entitled "Blood Bags Having an Insert Member", which application is assigned to the assignee of this application.

The initial research, however, also indicated that the addition of quantities per se of the liquid ester material such as di-2-ethylhexylphthalate to the blood container did not exhibit the anti-hemolytic effect obtained when the ester material is incorporated into the plastic material of the blood container or an insert within the container. Attempts to emulsify the ester material were also unsuccessful, resulting in emulsions that were basically unstable.

By this invention, it has been surprisingly found that stabilized emulsions of anti-hemolytic agents as described herein provide further significantly improved anti-hemolytic effect, when placed in the presence of stored blood, to make it possible to even reduce the hemolysis of stored blood to less than that which is conventional for the commercially-available, ester-plasticized polyvinyl chloride blood bags. The emulsion may be stabilized in accordance with this invention by a specific technique as described below.

DESCRIPTION OF THE INVENTION

In accordance with this invention, blood may be stored in vitro for a period of more than two days at a reduced temperature in a hemocompatible container, which also contains a sufficient quantity of an emulsion of an anti-hemolytic agent, for example, a fatty ester containing at least two ester linkages comprising fatty hydrocarbon groups of four to twelve carbon atoms each, with the ester linkages being preferably spaced closer together than the 1,3 relation, to cause a reduction in the hemolysis of the stored blood, when compared with blood under similar storage conditions in the absence of the emulsion.

Preferably, the emulsion contains the above fatty ester as an antihemolytic agent and emulsified with a sufficient quantity of a hemocompatible surfactant to stabilize the emulsion for a period of time, at least equal to the duration of storage of the blood. Of course, indefinitely stable emulsions are preferred. Such emulsions may generally be made by mixing the anti-hemolytic agent, for example the above-described fatty ester, with the hemocompatible surfactant in the substantial absence of water. After intimate mixing, the resulting material is added to the water ingredient to form the emulsion, which may be indefinitely stable, contrary to the results with other emulsification techniques.

The fatty hydrocarbon groups in the ester linkage

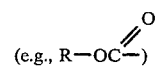

(e.g., R—OC—)

are preferably alkyl radicals of 4 to 12 carbon atoms. The ester linkages are preferably spaced closer than the 1,3 relation, by which is meant that the ester linkages are preferably bonded to the same or adjacent carbon or other atoms such as phosphorus. Most preferably, fatty ester linkages which are bonded adjacent to carbon atoms, or the same phosphorous atom, appear to be the most active in their anti-hemolytic effect, but fatty ester linkages which are separated farther apart on highly mobile hydrocarbon chains can also be very active, for example linear alkylene chains, forming compounds such as di-2-ethylhexyladipate, which tend to diminish in activity as the ester groups are spaced farther apart than in that compound. Preferably, such linear hydrocarbon chains contain no more than 8 carbon atoms, excluding the ester linkage carbon atoms. Also, maleate esters and related materials are active.

It is also preferable for the preferred organic radicals of the ester linkages to be alkyl of 7 to 10 carbon atoms, e.g., octyl groups, for example N-octyl, heptyl, nonyl, decyl, or 2-ethylhexyl. However, other radicals such as hexyl or dodecyl may also be used. Also, similar alkenyl radicals such as octenyl, nonenyl, or decenyl containing one or more unsaturated linkages may be used.

Examples of these preferred ester materials are the various dioctyl phthalates and dioctyl adipates, dioctyl maleates, and trioctylphosphate, which of course is an ester of phosphoric acid. Other anti-hemolytic agents which may be used include tri-functional esters such as tri-ethylhexyl trimellitate or other trioctyltrimellitate, and other esters in which the fatty acid groups are not adjacent on the carbon atoms such as dioctylterephthalate.

Generally, the antihemolytic agent may be rendered effective by bringing it into contact with the stored blood in a highly dispersed manner, so that a diffusion exchange may slowly take place between the antihemolytic agent and the blood. The emulsions used herein are preferred because, through them, precisely controlled amounts of the antihemolytic agents may be added to the blood, to provide a concentration in the blood of preferably 50 to 100 parts per million. Other gross techniques of adding the antihemolytic agents to the blood may cause insufficient quantities of the antihemolytic agent to go into the blood phase, especially in the first few days of blood storage. On the other hand, gross excesses of the antihemolytic agent may be placed into the blood by uncontrolled techniques, such as coating the sides of the container with the antihemolytic agent prior to adding the blood to the container.

Any blood-compatible, non-toxic emulsifying agent may be used herein, for example, polysorbate 80 (as identified in the U.S. Pharmacapoeia), which is a complex mixture of polyoxyethylene ethers of mixed partial oleic esters of sorbitan anhydrides, sold for example as Tween 80 by I.C.I. Americas, Inc. Another suitable material is sold by the same company under the name Tween 40, being polyoxythylene (20) sorbitan monopalmitate. Other examples of possible emulsifiers includes cholesterol and lecithin, which are advantageous, since they are normally found in the body.

In use, the emulsions of this invention may be inserted into a conventional blood bag in combination with a preservative-nutrient conventionally found in blood bags, such as CPD or ACD.

The examples below are offered for illustrative purposes only, and are not intended to limit the scope of the invention of this application, which is as defined in the claims below.

EXAMPLE 1

Emulsions were made of 2 ml. of Tween 80 (polysorbate 80), respectively with 2 ml. each of the following materials: di-2-ethylhexylphthalate, dioctylterephthalate, and tri-2-ethylhexyltrimellitate.

After mixing the Tween 80 with the respective ester materials, 0.3 ml. of each of the mixtures was added to separate portions of 150 ml. of sterile, 0.9 weight percent saline solution, with shaking, to form a stable emulsion.

One half ml. of each of these emulsions was added to separate polypropylene test tubes, along with 7.5 ml. of well-mixed, freshly drawn, whole human blood, anticoagulated with the known CPD material.

The blood was drawn from a human donor into a vinyl blood bag plasticized with tri-2-ethylhexyltrimellitate, which is a non-leachable plasticizer, to prevent the early contact of the blood with any leachable plasticizer.

The polypropylene test tubes were inverted twice after closing with stoppers, and refrigerated at 4° C. for 21 days.

Two control tubes included a tube only of blood as control No. 1, and a tube which contained blood and a corresponding concentration of the Tween 80 in saline solution, as control No. 2.

After the 21 days, the plasma hemoglobin content of each of the samples was determined with the results being as indicated in Table I below.

TABLE I

| Emulsion Sample Tested | Plasma Hemoglobin Content (mg./Deciliter) |
|---|---|
| Di-2-ethylhexylphthalate | 8 ± 1 |
| Dioctylterephthalate | 20 ± 2 |
| Tri-2-ethylhexyltrimellitate | 12 ± 1 |
| Control No. 1 | 26 ± 2 |
| Control No. 2 | 24 ± 1 |

EXAMPLE 2

Further blood samples were made for testing in the manner identical to that previously described in Example 1 above and stored for 28 days. The results were as indicated in the Table II below.

TABLE II

| Emulsion Sample Tested | Plasma Hemoglobin Content (mg./Deciliter) |
|---|---|
| Di-2-ethylhexylphthalate | 10 ± 1 |
| Dioctylterephthalate | 26 ± 1 |
| Tri-2-ethylhexyltrimellitate | 16 ± 1 |
| Control No. 1 | 32 ± 1 |
| Control No. 2 | 31 ± 1 |

It can be seen that the emulsions of all three of the ester materials exhibit an antihemolytic effect, with the di-2-ethylhexylphthalate exhibiting the strongest effect.

EXAMPLE 3

The experiment of Example 1 above was repeated, but substituting the surfactant Tween 40 for the Tween 80 of the previous example. Blood was processed and stored in similar manner with, respectively, an equal concentration of the emulsion containing, respectively, di-2-ethylhexylphthalate and tri-2-ethylhexyltrimellitate.

Table III below shows the plasma hemoglobin in the blood after respectively 21 days and 28 days of storage for each of the emulsions of the two different ester materials.

TABLE III

| | Plasma Hemoglobin (mg/Deciliter) | |
|---|---|---|
| Storage Time | Emulsion of Di-2-ethylhexylphthalate | Emulsion of Tri-2-ethylhexyltrimellitate |
| 21 Days | 9 ± 1 | 16 ± 1 |
| 28 Days | 12 ± 1 | 21 ± 1 |

The previous control results are believed to be effective for this experiment as well, since identical conditions were used except for the change of surfactant.

EXAMPLE 4

Emulsions were made of two ml. of Tween 80 (polysorbate 80), respectively with two ml. each of the ester materials as listed below in Table IV.

After mixing the Tween 80 with the respective ester materials, 0.2 ml. of each of the mixed materials was added to separate portions of 83 ml. of sterile, 0.9 weight percent saline solution, with shaking, to form a stable emulsion.

One half ml. of each of these emulsions was added to separate polypropylene test tubes, along with 7.5 ml. of well-mixed, freshly-drawn, whole human blood, anti-coagulated with the known CPD material.

The blood was drawn from a human donor in the manner previously described in Example 1. The polypropylene test tubes were inverted twice after closing with stoppers, and refrigerated at 4° C. for 21 days.

One control tube contained blood in a corresponding concentration of the Tween 80 in saline solution. Another control tube contained just blood, but also containing a strip of polyvinyl chloride plasticized with di-2-ethylhexylphthalate.

After 21 days, the plasma hemoglobin content of each of the samples was determined, with results being as indicated in Table IV below.

TABLE IV

| Emulsion Sample Tested | Plasma Hemoglobin Content (mg/Deciliter) |
|---|---|
| Tri-2-ethylhexylphosphate | 5 ± 1 |
| Diisononylphthalate | 7 ± 1 |
| Diisodecylphthalate | 8 ± 1 |
| Di-2-ethylhexylphthalate | 9 ± 2 |
| Tri-2-ethylhexyltrimellitate | 11 ± 1 |
| Di-2-ethylhexylmaleate | 14 ± 1 |
| Dihexylphthalate | 15 ± 3 |
| Di-2-ethylhexylisophthalate | 20 ± 2 |
| Didodecylphthalate | 18 ± 1 |
| Di-2-ethylhexylazelate | 19 ± 2 |
| Dibutylphthalate | 18 ± 2 |
| Control tube containing blood plus plasticized polyvinyl chloride containing di-2-ethylhexylphthalate | 16 ± 2 |
| Blank control without ester material | 24 ± 2 |

That which is claimed is:

1. The method of storing blood in vitro for a period of more than two days at a reduced temperature in a hemocompatible container which also contains a sufficient quantity of an emulsion of an antihemolytic agent emulsified with a blood-compatible, nontoxic surfactant emulsifying agent, said antihemolytic agent being a fatty ester containing at least two ester linkages comprising fatty hydrocarbon groups of four to twelve carbon atoms each, said emulsion being stabilized and blood hemolysis reduced for a period of time equal to the duration of storage of the blood, when compared with blood under similar storage conditions in the absence of said emulsion.

2. The method of claim 1 in which said hydrocarbon groups contain 7 to 10 carbon atoms.

3. The method of claim 1 in which said fatty ester comprises a pair of ester linkages bonded to a highly mobile hydrocarbon chain.

4. The method of claim 3 in which said highly mobile hydrocarbon chain is a linear alkylene chain.

5. The method of claim 4 in which said linear alkylene chain contains no more than eight carbon atoms, excluding the ester linkage carbon atoms.

6. The method of claim 1 in which said fatty ester is tri-2-ethylhexyltrimellitate.

7. The method of claim 1 in which the ester linkages are bonded to adjacent carbon atoms.

8. The method of claim 7 in which said ester material is a dioctylphthalate.

9. The method of claim 2 in which said fatty ester is trioctylphosphate.

10. The method of claim 2 in which said fatty hydrocarbon groups are selected from the group consisting of alkyl and alkenyl.

11. The method of mixing an antihemolytic agent ester composition containing at least two ester linkages comprising fatty hydrocarbon groups of four to twelve carbon atoms each with a quantity of blood-compatible, nontoxic surfactant emulsifying agent, mixing the resulting composition with water to form a stable emulsion of said ester composition, said emulsion being stabilized by said surfactant emulsifying agent, and thereafter storing blood in vitro for a period of more than two days at reduced temperature in a hemocompatible container which contains a sufficient quantity of said stable emulsion to cause a reduction in the hemolysis of the stored blood, when compared with blood under similar storage conditions in the absence of said emulsion stored for the same amount of time.

12. The method of claim 11 in which said fatty hydrocarbon groups contain 7 to 10 carbon atoms.

13. The method of claim 11 in which said fatty ester comprises a pair of ester linkages bonded to a highly mobile hydrocarbon chain.

14. The method of claim 13 in which said highly mobile hydrocarbon chain is a linear alkylene chain.

15. The method of claim 14 in which said linear alkylene chain contains no more than eight carbon atoms, excluding the ester linkage carbon atoms.

16. The method of claim 11 in which said fatty ester is tri-2-ethylhexyltrimellitate.

17. The method of claim 11 in which the ester linkages are bonded to adjacent carbon atoms.

18. The method of claim 17 in which said ester material is selected from the group consisting of dioctylphthalates and dioctyladipates.

19. The method of claim 11 in which said fatty ester is trioctylphosphate.

20. The method of claim 12 in which said fatty hydrocarbon groups are selected from the group consisting of alkyl and alkenyl.

21. A blood storage container made of a hemocompatible material, said container also including a sufficient quantity of an emulsion of an antihemolytic agent emulsified with a blood-compatible, nontoxic surfactant emulsifying agent, said antihemolytic agent being a fatty ester containing at least two ester linkages comprising fatty hydrocarbon groups of four to twelve carbon atoms each, said emulsion being stabilized and blood hemolysis reduced for a period of time equal to the duration of storage of the blood, when compared with blood under similar storage conditions in the absence of said emulsion.

22. The container of claim 21 in which said fatty hydrocarbon groups contains 7 to 10 carbon atoms.

23. The container of claim 21 in which said fatty ester comprises a pair of ester linkages bonded to a highly mobile hydrocarbon chain.

24. The container of claim 23 in which said highly mobile hydrocarbon chain is a linear alkylene chain.

25. The container of claim 24 in which said linear alkylene chain contains no more than eight carbon atoms, excluding the ester linkage carbon atoms.

26. The container of claim 21 in which said fatty ester is tri-2-ethylhexyltrimellitate.

27. The container of claim 21 in which said ester linkages are bonded to adjacent carbon atoms.

28. The container of claim 22 in which said fatty hydrocarbon groups are selected from the group consisting of alkyl and alkenyl.

29. A blood bag made of hemocompatible plastic which contains an amount of a stable emulsion made of a antihemolytic agent selected from the group consisting of a dioctyl phthalate and a trioctyltrimellitate in the presence of sufficient non-toxic, hemocompatible surfactant to stabilize the emulsion, said blood bag also containing a blood nutrient and stabilizing agent.

30. The container of claim 29 in which said surfactant is selected from the group consisting of cholesterol and lecithin.

31. A blood storage container made of a hemocompatible material, said container also including sufficient quantity of an emulsion of an antihemolytic agent ester material containing at least two ester linkages comprising fatty hydrocarbon groups each of 6 to 12 carbon atoms, said ester linkages being spaced closer than 1,3 relation, said emulsion being stabilized by the presence of a non-toxic, hemocompatible surfactant, said emulsion being present in sufficient amount to cause a reduction in the hemolysis of blood stored in said container for a period of 21 days, when compared with blood under similar storage conditions in the absence of said emulsions, said blood bag also containing a blood nutrient and stabilizing agent.

32. The container of claim 31 in which said surfactant is selected from the group consisting of cholesterol and lecithin.

33. The container of claim 31 in which said ester is dioctylphosphate.

34. The blood storage container of claim 31 in which said fatty hydrocarbon groups are alkyl.

* * * * *